(12) United States Patent
Barnes et al.

(10) Patent No.: US 6,702,459 B2
(45) Date of Patent: Mar. 9, 2004

(54) MOBILE RADIOGRAPHY SYSTEM AND PROCESS

(75) Inventors: Gary T. Barnes, Birmingham, AL (US); David T. Gauntt, Homewood, AL (US)

(73) Assignee: The UAB Research Foundation, Birmingham, AL (US)

( * ) Notice: Subject to any disclaimer, the term of this patent is extended or adjusted under 35 U.S.C. 154(b) by 44 days.

(21) Appl. No.: 10/121,367

(22) Filed: Apr. 11, 2002

(65) Prior Publication Data

US 2002/0150215 A1 Oct. 17, 2002

Related U.S. Application Data

(60) Provisional application No. 60/282,978, filed on Apr. 11, 2001.

(51) Int. Cl.[7] ................................................ H05G 1/02
(52) U.S. Cl. ........................ 378/197; 378/193; 378/198; 250/522.1
(58) Field of Search ................................ 378/197, 193, 378/198; 250/522.1

(56) References Cited

U.S. PATENT DOCUMENTS

| | | | |
|---|---|---|---|
| 4,752,948 A | | 6/1988 | MacMahon |
| 4,885,761 A | * | 12/1989 | Sones et al. ............. 250/360.1 |
| 5,241,578 A | | 8/1993 | MacMahon |
| 5,388,143 A | | 2/1995 | MacMahon |
| 5,499,284 A | * | 3/1996 | Pellegrino et al. .......... 378/198 |
| 6,155,713 A | * | 12/2000 | Watanabe ................... 378/197 |
| 6,491,429 B1 | * | 12/2002 | Suhm ........................ 378/205 |

OTHER PUBLICATIONS

Niklason, LT, Sorenson, JA, Nelson, JA; Scattered Radiation in Chest Radiography; *Med. Phys.* 8:677–681, 1981.
Press, WH, Flannery, BP, Teukolsky, SA, Vetterling, WT; Numerical Recipies in C: The Art of Scientific Computing; Cambridge University Press, Cambridge UK, 1988.
Niklason, LT, Barnes, GT, Carson, P; Accurate Alignment Device for Portable Radiography; *radiology* 173(P):452, 1989.
Barnes, GT; Contrast and Scatter in X-ray Imaging; *Radiographics*; 11:307–232, 1991.
O'Donovan, PB, Skipper, GJ, Litchney, JC, Salupo, AJ, Bortnick, JR; Device for Facilitating Precise Alignment in Bedside Radiography; *Radiology* 184:284–285, 1992.
Tucker, DM, Souto, M, Barnes, GT; Scatter in Computed Radiology; *Radiology*; 188:271–274, 1993.

* cited by examiner

Primary Examiner—Edward J. Glick
Assistant Examiner—Courtney Thomas
(74) Attorney, Agent, or Firm—Bradley Arant Rose & White, LLP

(57) ABSTRACT

Disclosed is a mobile radiographic unit with improved x-ray scatter control. Improved x-ray scatter control is provided through the alignment of the system with the focal line of an anti-scatter grid. In a preferred embodiment, the system comprises an x-ray source assembly, a tube housing mounting, an automatic measuring means, a motion control means and a processing means in communication with the automatic measuring system and the motion control system. The alignment of the system occurs with minimal input by the operator.

53 Claims, 14 Drawing Sheets

MOBILE RADIOGRAPHY SYSTEM AND PROCESS

FIELD OF THE INVENTION

This application claims priority to U.S. patent application Ser. No. 60/282,978, which was filed on Apr. 11, 2001 and which is incorporated herein by reference. The present disclosure relates to radiography and, more particularly, to mobile radiography with improved x-ray scatter rejection.

BACKGROUND OF THE INVENTION

In the hospital setting, mobile radiographic exams are performed on patients that are incapable of being moved, or are difficult to move. In tertiary care medical centers, mobile radiographic exams represent a significant percentage of the radiographic exams performed. X-rays passing through an object, such as a human body, experience some degree of scatter associated with interactions with atoms or electrons. The primary x-rays transmitted through an object travel on a straight line path from the x-ray source (also referred to herein as the x-ray focal spot) to the image receptor and carry object density information. Scattered x-rays form a diffuse image that degrades primary x-ray image contrast. In thick patients, scattered x-ray intensity exceeds the intensity of primary x-rays. Scattering phenomena is well known and routinely compensated for in general radiography, fluoroscopy and mammography through the use of anti-scatter grids.

An anti-scatter grid includes a laminate of lead foil strips interspersed with strips of radiolucent material (FIG. 1). The grid is positioned between the object of interest and the x-ray image receptor plate and oriented such that the image forming primary x-rays are incident only with the edges of the lead foil strips. Thus, the majority of primary x-rays pass through the radiolucent spacer strips. In contrast, scattered x-rays are emitted in all directions after interaction with the object and as such, scattered x-rays are incident on a larger area of the lead strips and only a small percentage of scattered x-rays are transmitted by the grid, as compared to primary x-rays. The degree of scatter control for a given grid depends upon the grid ratio, which is defined as the ratio of the radiopaque strip thickness in the direction of the x-ray path to the width of the radiolucent spacer material as measured orthogonal to the x-ray beam path. Thus, the higher the grid ratio, the greater the scatter control. A high grid ratio, while more effective, is also more difficult to align relative to a focal spot. In order to compensate for x-ray beam divergence in a focused grid, the radiopaque strips are tilted to a greater extent with increasing distance from the center of the grid. The planes of the grid vanes all converge along a line known as the focal line. The distance from the focal line to the surface of the grid is referred to as the focal length of the grid. The focal line coincides with the straight line path to the focal spot (illustrated in FIG. 2). Thus, when the focal spot is coincident with the focal line of the grid, the primary x-rays have minimal interaction with the radiopaque lead strips and maximal primary transmission is obtained. Misalignment of the focal line of the anti-scatter grid with the focal spot diminishes primary x-ray transmission while scattered x-ray transmission remains unchanged. Thus, optimal primary x-ray transmission requires alignment (positional and orientational) of the focal spot with the focal line of the anti-scatter grid.

In general radiography, fluoroscopy and mammography, the image receptor and x-ray tube are rigidly mounted and in a fixed position relative to one another, thereby making focal spot and grid alignment a simple process. In mobile radiography, an image receptor is placed under a bedridden patient and the x-ray source is positioned above the patient. Since the relative separation of the focal spot and the image receptor is variable, determining the proper position and orientation of an anti-scatter grid between a patient and the image receptor becomes a difficult alignment problem. If a grid is not used, only a small fraction of the possible contrast is obtained in the x-ray image. As a result, scatter to primary x-ray ratios of 10:1 or more are common in chest and abdominal bedside radiography resulting in less than 10% of the possible image contrast being obtained in mobile radiographic films ([1,2]Barnes, G T, RadioGraphics 11:307–323, 1991; Niklason et al., Med. Phys. 8:677–681, 1981). Contrast limitations are exacerbated if digital storage phosphor image receptors are utilized in place of the more conventional screen-film systems ([3]Tucker et al., Radiology 188:271–274, 1993).

When grids are utilized in conjunction with mobile radiography, the grid is typically not aligned. Misalignment problems are diminished by utilizing a grid having a low ratio of 8:1 or less. Although x-ray image contrast is improved with the use of a low ratio grid, the contrast remains significantly lower than otherwise could be obtained with a properly aligned, high ratio grid having a grid ratio of 10:1 or greater.

Thus while mobile radiography is in many ways more convenient than fixed installation radiography, its clinical utility is diminished due to the inferior image quality caused by scattered radiation which is a greater problem in mobile radiography due to the difficulty in producing the proper alignment of the focal spot with the anti-scattering grids. A means to produce proper alignment that is easy for the operator to use would significantly improve mobile radiographic image contrast and image quality, and thus increase the clinical utility of mobile radiography.

A system is disclosed in U.S. Pat. No. 4,752,948 which includes a rigid arm mounted on the grid tunnel, with a coupling on the other end that connected to the x-ray source housing. A hinge on the grid end of the arm allowed it to be folded for transportation. A radiography technologist unfolds the arm, locks the hinge, slides the grid tunnel and film cassette under the patient, and attaches the x-ray source housing to the other end of the arm. The arm then holds the x-ray source rigidly in alignment with the grid tunnel. This system demonstrated the image quality and clinical advantages of employing properly aligned high ratio grids in bedside radiography. However, difficulty in using the system limited the application thereof in mobile radiography.

Loren Niklason et al. disclosed a mobile radiography system utilizing a telescoping arm ([4]Niklason et al., Radiology 173(P):452, 1989). One end of the arm was permanently attached to the mobile x-ray unit column and the other end was attached by the radiography technologist to the grid assembly after the grid and cassette were positioned under the patient and the mobile unit was centered right-to-left to the grid assembly. Dials indicated to the technologist the transverse direction the tube needed to be moved and the angle the tube had to be rotated to align it with the grid. The time consuming and complex steps to align the x-ray tube using this system limited the application thereof in mobile radiography.

U.S. Pat. Nos. 5,241,578 and 5,388,143 disclose a laser alignment device that required a user to align a laser and a mark in the alignment light field with a reflector device that mounted on a corner of a grid tunnel. As with Niklason's system, this system required the user to manually align the x-ray source by trial and error. Further, it required that part of the grid tunnel extend past the patient, which limited the application thereof in portable radiography.

Peter O'Donovan et al. disclosed a system involving electronic levels on the grid tunnel and source housing, an alignment target attached to the source, and crosshairs in the alignment light field ([5]O'Donovan et al., *Radiology* 184:284–285, 1992). A tape measure was used to ensure that the source was the proper distance from the grid tunnel. The user rotated the source housing until the two levels indicated that the central axis of the source was normal to the grid tunnel in one direction; turn on the collimator light; and move the tube housing until the shadow of one of the cross-hairs fell on a mark on the grid tunnel. The complexity of this procedure limited the application thereof in mobile radiography.

The prior art systems have been limited in their utility in clinical acceptability owing to the considerable additional effort required on the part of a radiography technologist to align the x-ray source. Thus, there exists a need for a mobile radiography system having a simple means to place the focal spot and the central x-ray beam in correct alignment (position and orientation) with regard to the anti-scattering grid.

DETAILED DESCRIPTION

The present disclosure provides a device and method to increase x-ray scatter control of mobile radiography equipment through optimal alignment of a focal spot with the focal line of an anti-scatter grid. A mobile radiography device and method according to the present disclosure affords a rapid and accurate alignment between a mobile radiographic device focal spot and the focal line of an anti-scattering grid. In a preferred embodiment, the present disclosure describes a system comprising an x-ray source assembly, an automatic measuring means, a motion control means and a processing means. The automatic measuring means utilizes a detecting means attached to a mobile radiographic system to determine the position and orientation of the grid tunnel relative to the radiographic system by reference to a target array or other external object, a processing means to determine the position and orientation of the anti-scatter grid relative to the a fixed point on the system, as well as the alignment of the focal spot and central x-ray beam relative to the anti-scattering grid for production of an optimal image, and driving means in communication with the processing means to position the x-ray focal spot to a state of alignment relative to the focal line of an anti-scattering grid. It is preferred that a high ratio anti-scattering grid be employed. For the purpose of this specification, a high ratio anti-scattering grid is defined as a grid having a grid ratio of 10:1 or greater. Through the device and method of the present disclosure, the process of positioning the components of a mobile radiographic system to a state of alignment is automated with minimal operator involvement.

Figure 1:
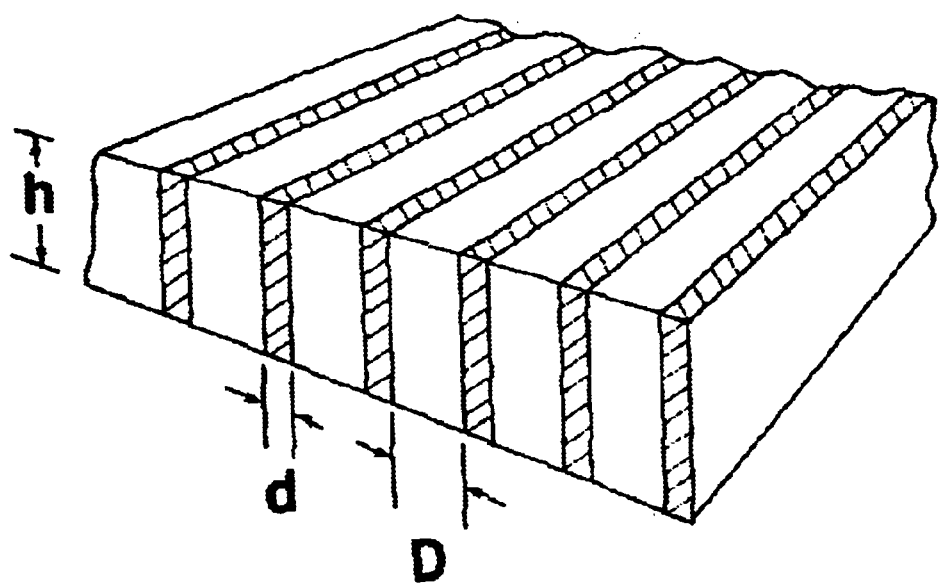
FIG. 1 is a schematic view of an anti-scattering grid common in the field.
Figure 2:
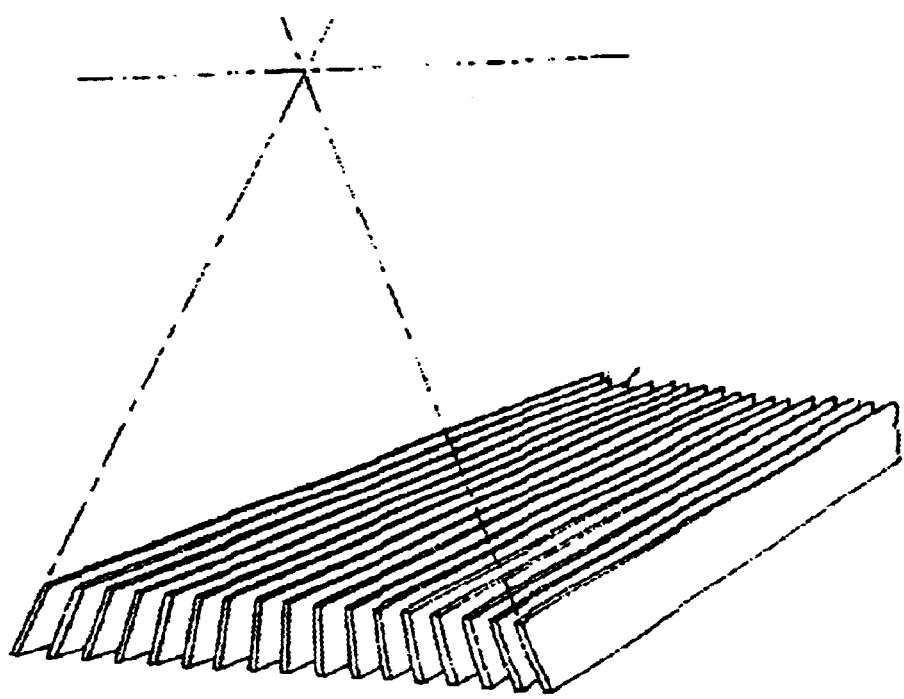
FIG. 2 is a schematic view of a focused anti-scattering grid common in the field.
Figure 3:
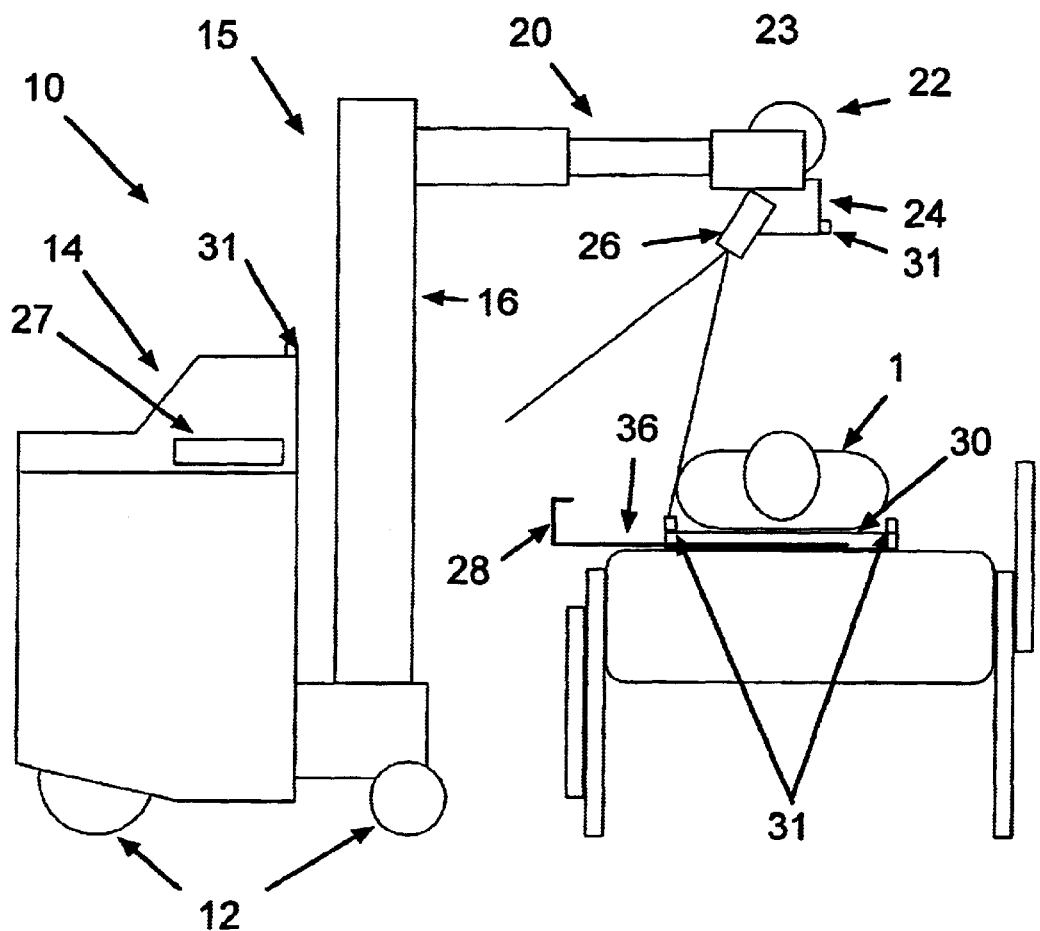
FIG. 3 is a side view of a mobile radiography system according to the present disclosure.

Referring now to FIG. 3, a mobile x-ray generator system 10 includes a wheeled base 12, an operator's console 14, an x-ray source assembly and a tube housing mounting. The x-ray source assembly preferably has at least one degree of freedom of motion and comprises an x-ray tube housing 22 containing an x-ray source, the tube housing 22 having an x-ray emission aperture (not shown), and a collimator 24 attached to the tube housing 22 and aligned with the x-ray emission aperture. The tube housing mounting has a plurality of degrees of freedom of motion to allow the x-ray source assembly to be positioned at a desired position and orientation. In one embodiment, the tube house mounting comprises an adjustable, vertical column 16, an adjustable, horizontal arm 20 mounted to the column 16 and an adjustable gimbal 23 for coupling the tube housing 22 to the arm 20.

Figure 6A:
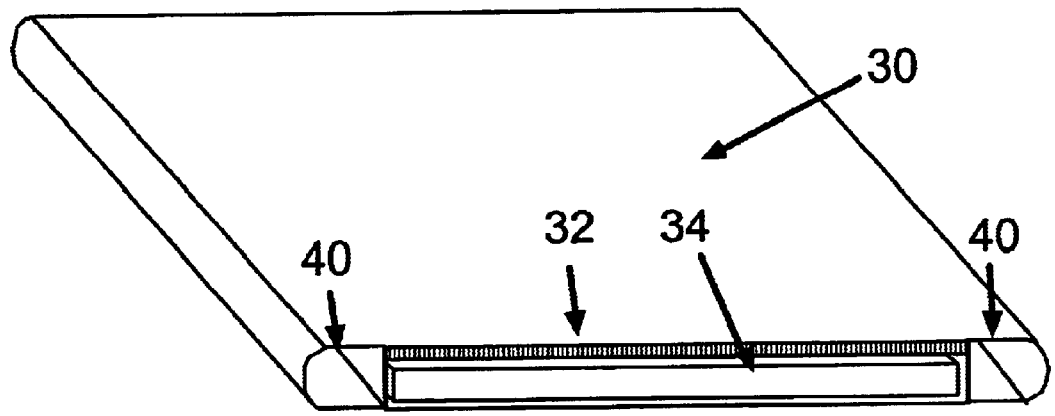
FIGS. 6A and 6B are perspective views of a grid tunnel of the present disclosure.
Figure 6B:
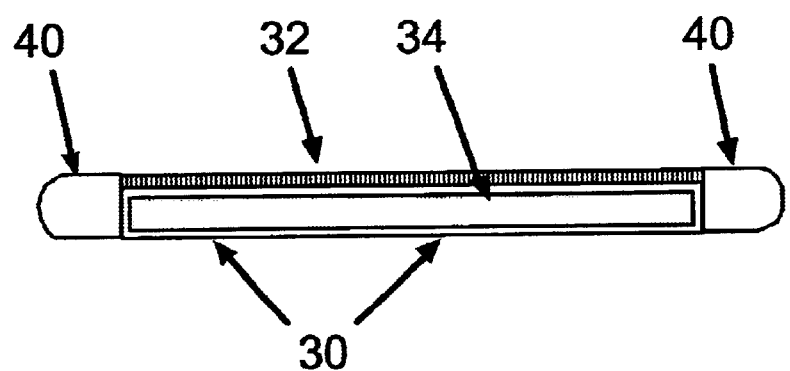

The mobile system 10 further comprises a processing means, a detecting means (described above as a camera 26) in communication with the processing means and the grid tunnel 30 with rigid arm 36 equipped with a target array 28 comprising a plurality of fiducial markers 50. A detecting means, illustrated in FIG. 3 as an optical detector, specifically as a digital camera 26, is attached to the system 10, preferably on collimator 24. The camera 26 is positioned to produce an image of a target array 28 and its fiducial markers 50 attached to the grid tunnel 30. The image produced by the detecting means may be any information that allows the processing means to determine the position of the fiducial markers 50. The grid tunnel 30 incorporates an anti-scattering grid 32 and contains a cavity to receive an image receptor 34 (illustrated in FIGS. 6A and 6B). An object to be imaged 1 is interspersed between the collimator 24 and the grid tunnel 30. An x-ray image receptor 34 is placed proximal to anti-scattering grid 32 and distal from an object, such as a patient 1.

The processing means analyzes images of the target array 28 acquired by the detecting means to determine the position and orientation of the target array 28 (which is equivalent to the position and orientation of the anti-scatter grid 32) relative to the detecting means, illustrated as camera 26

(which is equivalent to the position and orientation of the focal spot when the detecting means is positioned on the collimator 24). The processing means then calculates the optimal position and orientation of the x-ray tube housing 22 such that the focal spot and central ray are in a state of alignment with regard to the anti-scattering grid 32. The driving means (not shown) located within the mobile x-ray system 10 are directed by the processing means to position the system to the state of alignment.

Figure 4:
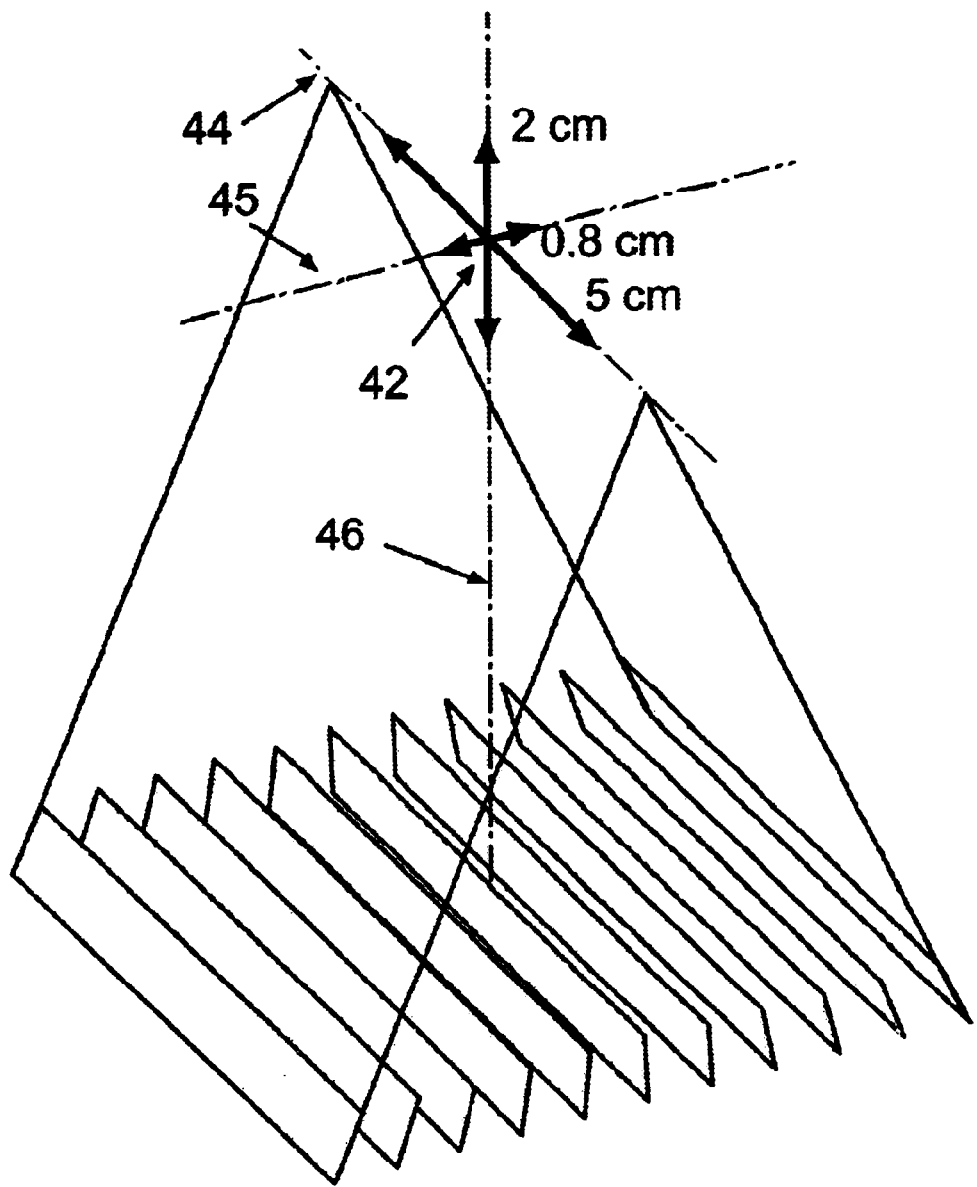
FIG. 4 is an illustration of the optimal and acceptable state of alignment for the mobile radiographic system of the present disclosure.

Referring to FIG. 4, the preferred location 42 of the focal spot is the intersection of the focal line 44 of the grid and a line 46 normal to the surface of the grid that passes through the center of the grid. This location is defined as the optimal focal spot position, and when the focal spot is in this location the transmission of x-rays through the anti-scatter grid is at its maximum value. The x-ray source assembly is in its preferred orientation when the central ray of the x-ray beam passes through the center of the grid, and the long and short axes of the x-ray beam are parallel to the long and short axes of the grid tunnel. When the x-ray focal spot is in its preferred location 42 and the x-ray source assembly is in its preferred orientation, then the system is defined to have optimal alignment.

The focal spot is in an acceptable position if the transmission of primary x-rays through the grid is at least 90% of the its maximum value over the entire grid, and if the focal spot is within 5 cm of its ideal location in a direction parallel to the focal line 44. For example, for a standard size 12:1 grid with a focal length of 100 centimeters, the focal spot position will be acceptable if it is on the focal line 44 and within 5 centimeters from the optimal location 42, on the normal line 46 and within 2 centimeters from the optimal location 42, or on a line 45 normal to both grid focal line 44 and the grid normal line 46 and within 0.8 centimeters of the optimal location 42. Similarly, the x-ray source assembly is in an acceptable orientation if the central ray of the collimated x-ray beam passes substantially close to the center of the grid, and the long and short axes of the collimated x-ray beam are substantially parallel to the long and short axes of the grid tunnel. When the x-ray focal spot is an acceptable position, and the x-ray source assembly is in an acceptable orientation, the system is defined to have acceptable alignment.

While it is preferred that the detecting means be affixed to the collimator housing 24, it is appreciated that the detecting means according to the present disclosure can be mounted in a variety of positions on a mobile x-ray system 10 to provide position and orientation data for control of the x-ray tube housing 22 position adjustment. It is further recognized that other detecting means in addition to a digital camera are operative herein. These additional detecting means may be optical in nature, or be based on other principles such as magnetic interactions, ultrasound, or inertial navigation. Some of these means mat not require the target arms 28, but may directly detect the grid tunnel 30, or fiducial markers attached directly to the grid tunnel.

In operation according to the present disclosure, grid tunnel 30 is placed under an imaging object 1, such as a hospital patient. A radiological technician thereafter attaches the rigid arm 36 to the grid tunnel 30. The arm 36 fits into a socket 40 on grid tunnel 30 and extends past the lateral dimensions of the object 1. Thus, the end of the arm 36 is visible to the detecting means, in this case camera 26. The operator places the detecting means in rough alignment with the target array 28. The rough alignment process may be aided by the use of a positioning means on the detecting means, such as a light, that will assist the operator in aligning the system properly. After the rough alignment, the automatic measuring system (AMS) is activated by the operator. The detecting means collects an image of the target array 28 and delivers the data to the processing means. The processing means calculates the position and orientation of the target array 28, and therefore the anti-scatter grid 32, relative to the detecting means, and therefore the focal spot when the detecting means is located on the collimator. Once the AMS calculates the relative position and orientation information, the operator activates the motion control system (MCS). On activation of the MCS, the processing means then directs the drive means to move the system to a state of alignment as determined by the AMS. The detecting means may collect a confirmatory image of the target array 28 to assure proper alignment of the system.

The mobile system 10 may be equipped an indicating means to alert the operator of the condition of the system 10. For instance, the indicating means could be a plurality of indicator lights, such as LED lights. If three indicator lights are used, one light could indicate the detecting means is unable to "see" all the fiducial markers 50 of the target array 28, two lights could indicate the detecting means "sees" all the fiducial markers 50, but is not yet aligned, and a third light could indicate the system is ready for use. The indicating means could also be a display panel to graphically display information regarding the condition of the system to the operator. In addition, the system 10 may have at least one control means, such as a button, toggle switch or similar device, on the system 10, preferably on the collimator handles. One control means will release the drive means and allow the operator to roughly align the tube housing 22 with the target array 28. Another control means will activate the MCS. The operator will be required to continually depress the control means for the MCS to remain active (referred to as a dead-man switch). If the control means is released during any point at which the tube housing 22 is under control of the MCS, the MCS stops immediately. This is a safety precaution designed to prevent the tube housing 22 or other parts of the system 10 from hitting nearby objects, such as intravenous stands or sensitive medical equipment.

Figure 5:
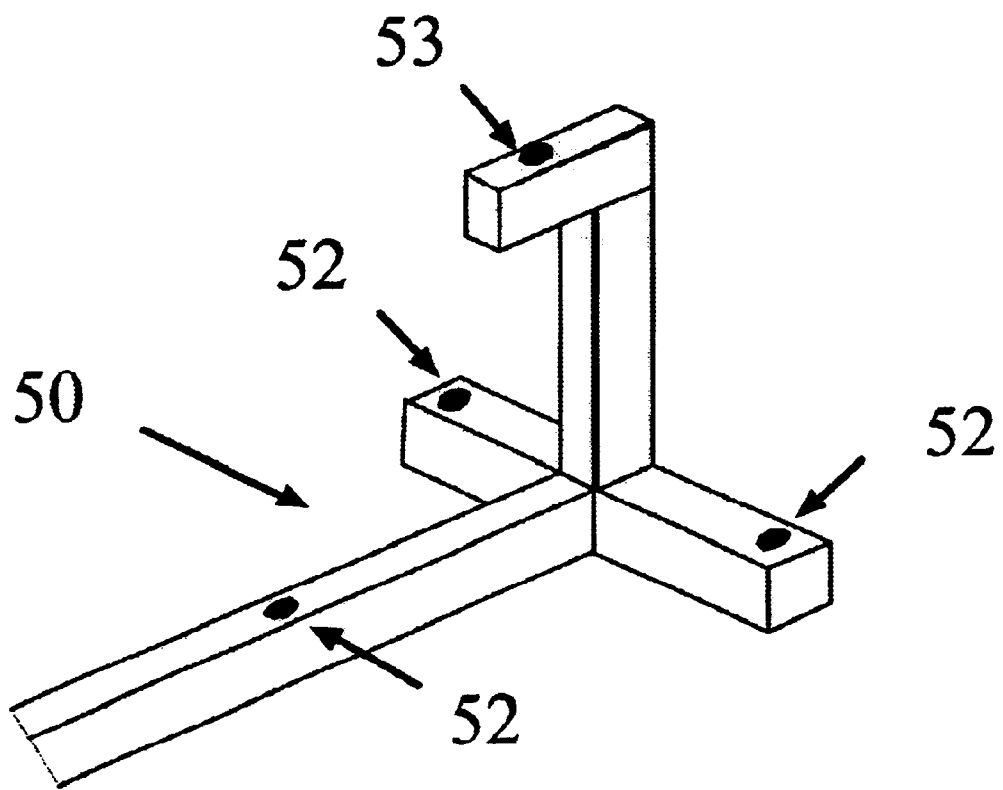
FIG. 5 is a perspective detail view of a target arm and fiducial markers according to the present disclosure.

The grid tunnel 30 and the rigid arm 36 are shown with greater clarity in FIGS. 5 and 6. The grid tunnel 30 is manufactured from material selected from the group including, but not limited to, rigid sheet metal, carbon fiber composites and impact resistant plastics, such as LEXAN (GE), polycarbonate, ABS and the like, or a combination of any of the above. It is preferred that the grid tunnel 30 is manufactured from carbon fiber composites. The grid tunnel 30 has sufficient strength to support the patient 1, and is typically designed to support more than 200 kilos. Preferably, the grid tunnel 30 has rounded edge surfaces 38 to facilitate insertion under the hospital patient 1. The arm 36 supports the target array 28, and may be constructed of the same materials as the grid tunnel 30. The arm 36 is adapted to insert within a channel 40 within the grid tunnel 30. Preferably, a channel 40 is provided along opposing edges of the grid tunnel 30 to accommodate transverse (parallel to the short axis of the grid tunnel) and longitudinal (parallel to the long axis of the grid tunnel 30) orientations of the grid tunnel under the patient 1. The arm 26 is preferably hollow to provide space for the electronic circuitry employed in the mobile system 10. The electronic circuitry allows the processing means to control the target array 28 (such as activating the fiducial markers 50 in a specific sequence) and allows the target arm to communicate with the processing means so the processing means can determine whether the target arm is in the transverse or longitudinal configuration.

This communication allows the processing means to adjust certain parameters of the system 10 (such as the collimator 24 settings). The communication can occur via wireless communications or through wires, however, wireless communication is preferred. This configuration of the target array (which is a proxy for the configuration of the anti-scattering grid 32 and the image receptor 40) is important in obtaining optimal image quality. The processing means will determine the configuration of the target arm and orientate the collimator 24 along the long axis of the grid tunnel 30 and adjust the collimator blade settings to adjust the width and length of the x-ray beam to the size and orientation of the image receptor. In addition, the channel 40 will have electrical contacts to determine when the arm 36 is fully inserted into channel 40. Optionally, a hand grip 42 is included in the grid tunnel 30 to facilitate crude alignment of the grid tunnel 30 beneath patient 1. Preferably, the target array 28 extends at least five inches beyond the track 40 to ensure visibility when a large patient 1 covers the grid tunnel 30.

FIG. 5 shows a target array according to the present disclosure having a plurality of fiducial markers 50, the position of the fiducial markers 50 being fixed relative to the grid tunnel 30, and therefore, to the anti-scatter grid 32. In the embodiment illustrated in FIG. 6, three markers 52 are provided in the plane of the anti-scattering grid 32 to provide a measure of the distance from the target array 28 to the detecting means (illustrated as camera 26), and therefore, the x-ray tube housing 22. A fourth marker 53 out of plane relative to the markers 52 provides a measure of transverse misalignment. In one embodiment, the fiducial markers are light emitting diodes (LEDs). When LEDs are used as the fiducial markers 50 of the target array 28, the detecting means collects images of the target array 28 with all the LEDs energized, all of the LEDs non-energized, and each of the four LEDs energized in succession. These images are analyzed by the automatic measuring system (as described below) and the images are converted to position and orientation information of the target array 28 relative to the detecting means. Alternatively, the fiducial markers 50 may be four differently colored LEDs and the detecting means may be a color digital camera. In this embodiment, the system can uniquely identify each of the LEDs with only the collection of two images corresponding to the energized and non-energized states.

In the embodiment described, a position and orientation measurement comprises the following steps. First, the detecting means, in this embodiment camera 26, acquires one or more images of the target array 28. The processing means analyzes these images to determine 6 parameters that describe the position and orientation of the target array 28 relative to the camera 26. This process is described diagrammatically in FIG. 9.

Figure 7:
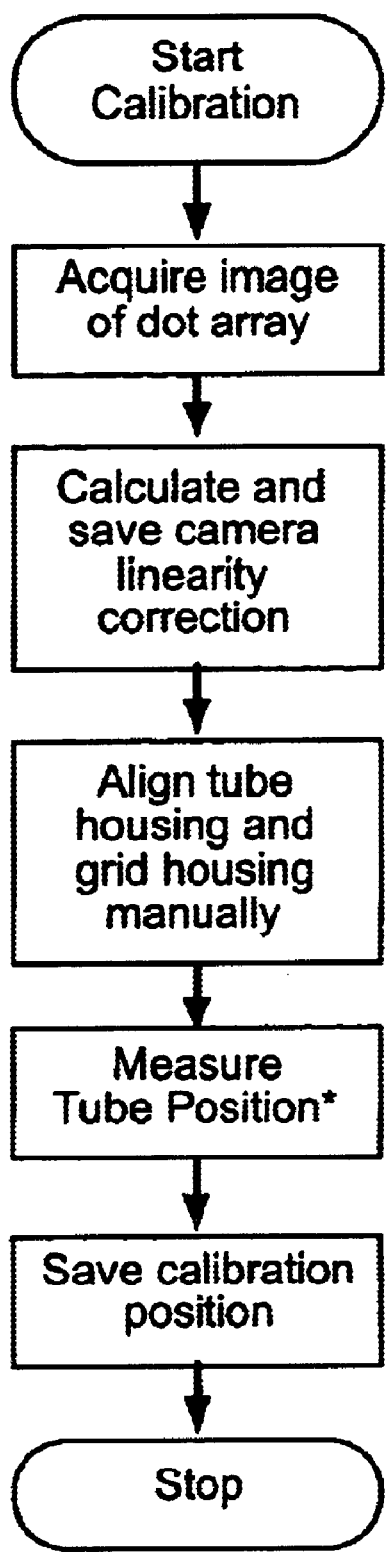
FIG. 7 is a flowchart illustrating the steps involved in the calibration procedure.
Figure 8:
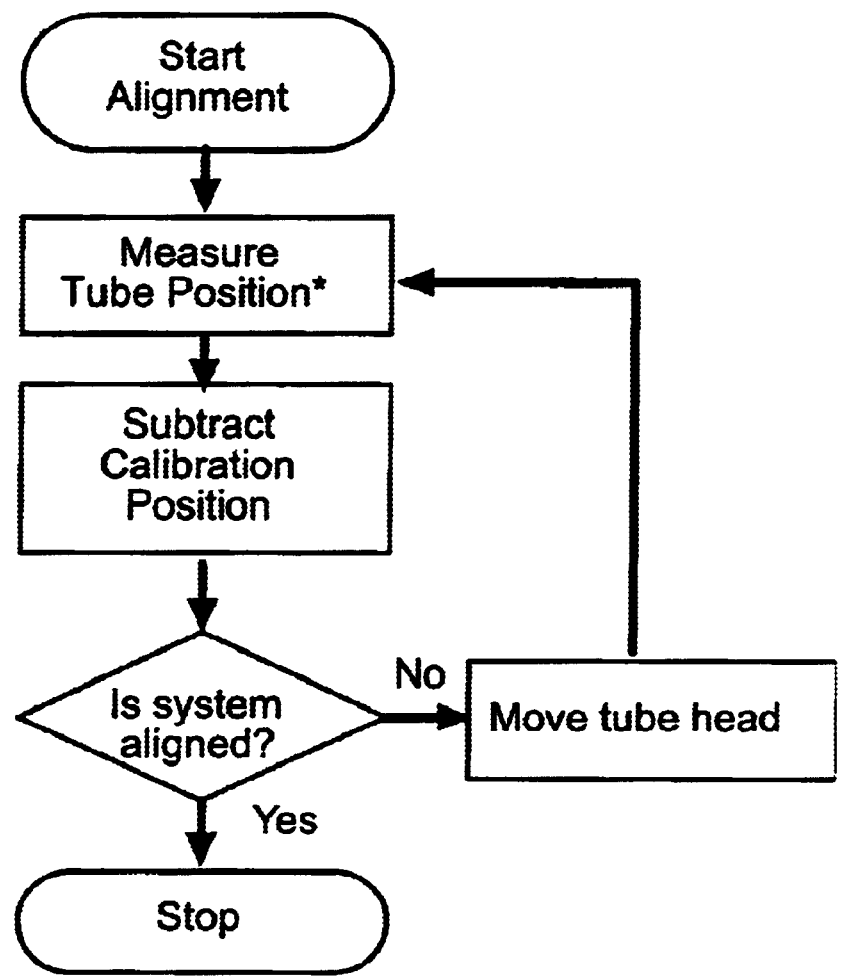
FIG. 8 is a flowchart illustrating the steps involved in the alignment procedure.

Before the system is used clinically, the mobile system 10 undergoes calibration. This calibration step need be performed just once for a given mobile system 10 and grid tunnel 30, as the calibration information is stored in a calibration file. The first step in the calibration is to generate a correction for the spatial non-linearity of the camera 26. This is accomplished by acquiring an image of a matrix of black dots, and fitting the measured position of the dots to a mathematical function. Next, the camera 26 is mounted on the collimator 24, the target arm 28 is mounted on the grid tunnel 30, and the tube housing 22 is positioned optimally so the x-ray focal spot falls on the focal line of the anti-scattering grid 32. The techniques involved in centering the focal spot are common the field and are within the ordinary skill of one in the art. The AMS then measures the position and orientation of the fiducial markers 50 on the target array 28 relative to the detecting means. The results of this measurement are stored in the processing means. The process is depicted diagrammatically in FIG. 7.

The first step in the clinical alignment procedure is to determine the position and orientation of the anti-scattering grid 32 relative to the tube housing 22 through the measurement of the position and orientation of the fiducial markers 50 on the target array 28. The processing means takes this position data and calculates the position of the tube housing 22 relative to the console 14 so that the tube housing 22 will be in a state of alignment relative to the anti-scattering grid 32, that is, the relative position stored during the calibration of the tube housing (described above). The processing means then directs the drive means of the MCS to move the tube housing 22 to this position so that the focal spot is in a state of alignment with the focal line of the anti-scattering grid 32. In summary, the AMS determines the position and orientation of the fiducial markers 50 of the target array 28 in relation to the x-ray tube housing 22, and uses this information to calculate a state of alignment for the system, and the MCS (under the control of the AMS) moves the system to the state of alignment.

Figure 14:
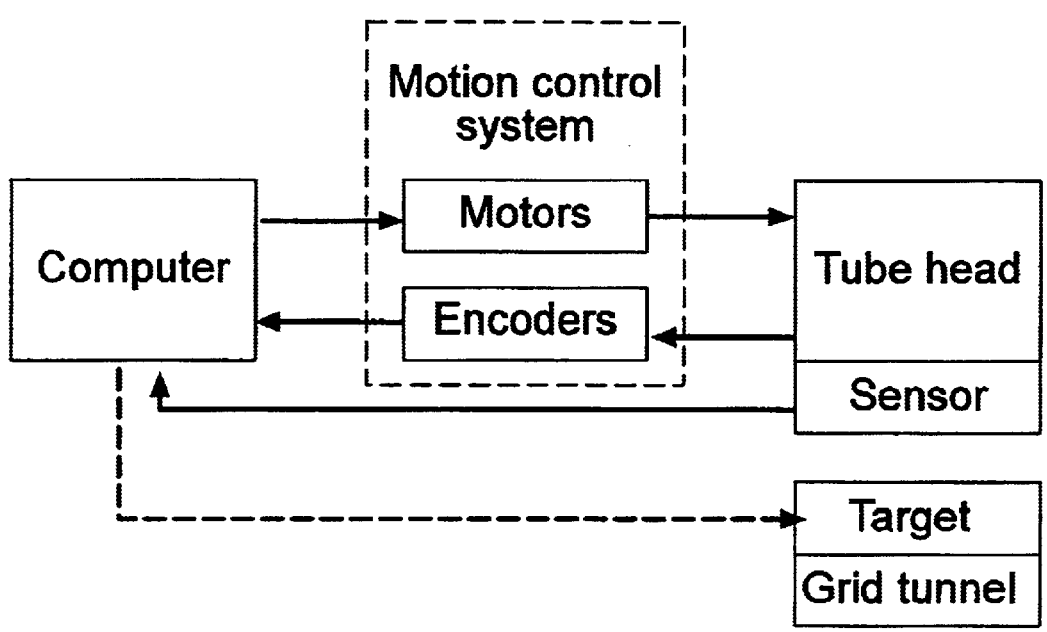
FIG. 14 is a flowchart illustrating the interaction between the automatic measuring system and the motion control system whereby the position of the x-ray source assembly relative to the console is determined. The arrowed lines indicate the flow of signals of controls. The dotted arrows indicate that the control function is optional.

The position and orientation of the x-ray source assembly has 6 degrees of freedom. Three degrees of freedom allow the x-ray source to move to the central position on the focal line of the anti-scatter grid 32, two degrees of freedom allow the x-ray source assembly to direct the central ray of the x-ray beam to the center of the anti-scatter grid 32, and one degree of freedom allows the collimator 24 to align with the long axis of the cassette (discussed in more detail below). The optimal alignment is achieved by the AMS and the MCS. The AMS measures 6 parameters that describe the Cartesian coordinate system of the target arm 28 (or grid tunnel 30) in relation to the Cartesian coordinate system of the camera 26 (or other detecting means). Encoders in the MCS measure 6 parameters that describe the Cartesian coordinate system of the collimator 24 in relation to the Cartesian coordinate system of the console 14. Comparing the MCS parameters to the AMS parameters, it is possible to determine the 6 parameters that describe the Cartesian coordinate system of the grid tunnel 32 in relation to the Cartesian coordinate system of the console 14, and therefore the 6 parameters that describe the optimal position and orientation of the tube housing 22 relative to the console 14. This flow of signals and/or controls is illustrated schematically in FIG. 14.

It is appreciated that an acceptable degree of alignment can be accomplished with fewer degrees of freedom in the MCS. For example, with three degrees of freedom the MCS could automatically move the focal spot to the center point on the focal line of the grid, aligning the focal spot with the grid. The user could then manually adjust the collimator orientation, achieving a result that is nearly as good as that obtainable with a six degree of freedom system. Similarly, the source assembly rotation adjustments which are generally small and less important can be done manually to further improve the alignment. In principle, the focal spot could be moved onto the focal line with as few as two degrees of freedom in the MCS, although with no guarantee that it would fall close to the line normal to the center of the grid. Such approaches align the source assembly and grid at the expense of more effort on the part of the user.

Figure 9:
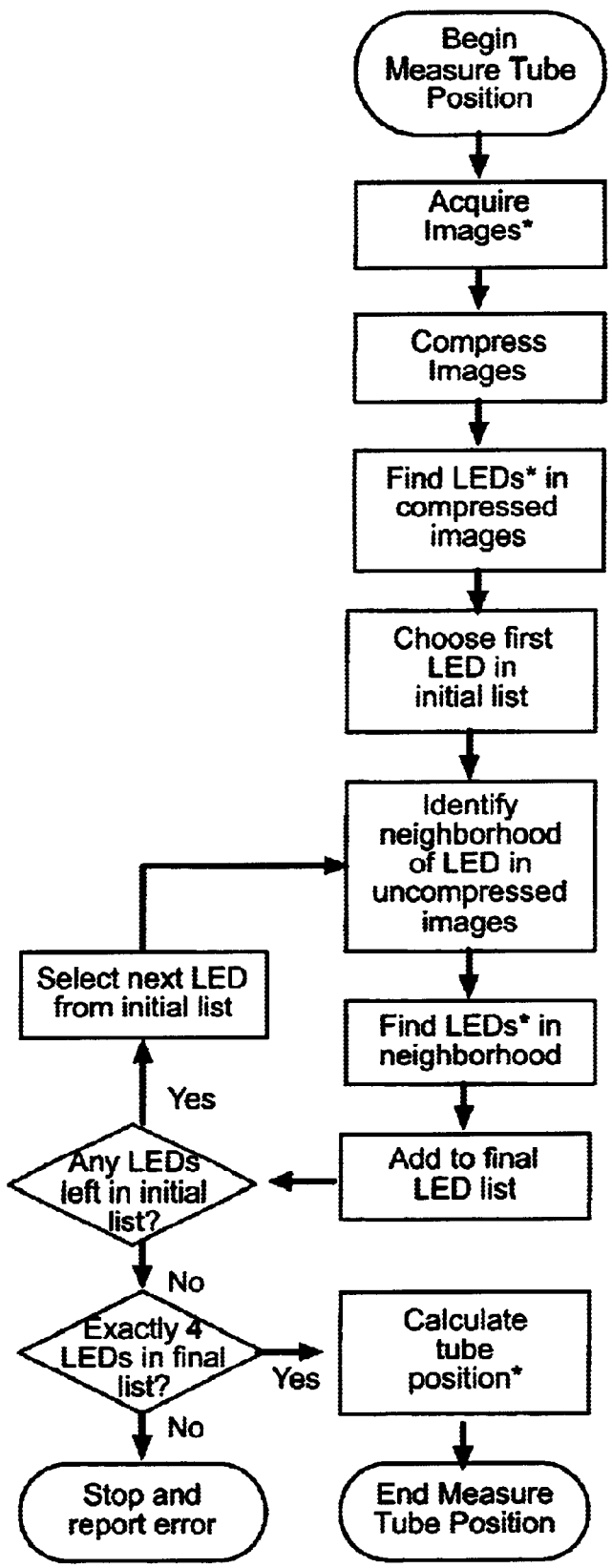
FIG. 9 is a flowchart illustrating the steps involved in measuring the position of the x-ray source assembly.

FIG. 9 diagrammatically illustrates one embodiment of the steps involved in measuring the tube position. An image is acquired from the camera 26 or other detecting means.

Figure 10:
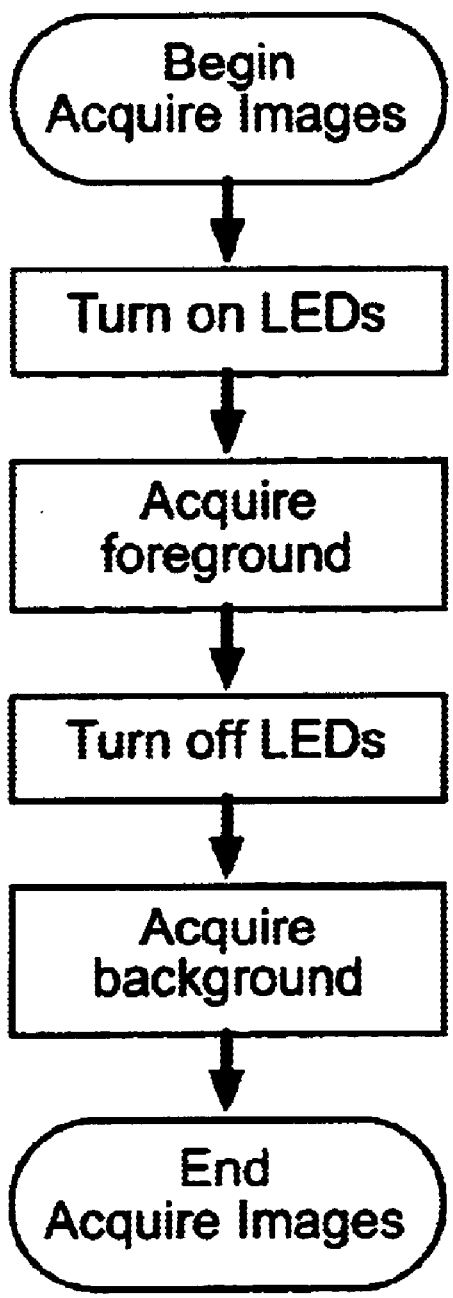
FIG. 10 is a flowchart illustrating the steps involved in acquiring an image of the target array.

FIG. 10 shows an example of the image acquisition process. As the acquisition process is initiated, all or some of the LEDs are turned on and a foreground image is obtained (in FIG. 10, assume all LEDs are illuminated). The LEDs are then turned off and a background image is acquired. The LEDs are controlled by the processing means as discussed above. The process may be repeated with less than all of the LEDS illuminated, and less than all of the LEDs turned off. In addition, the background image may be obtained before the foreground image, as the order of acquisition of the images is arbitrary.

Figure 11:
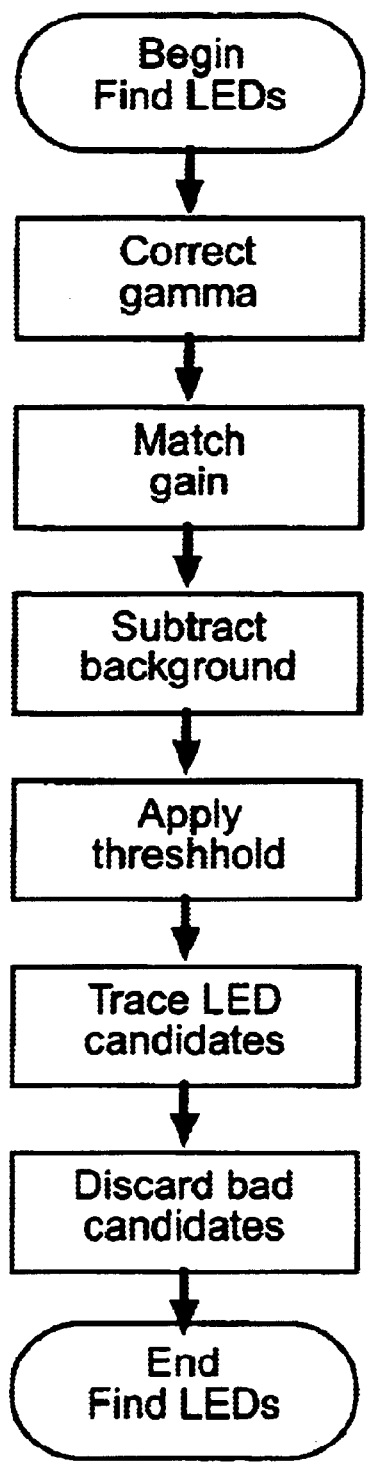
FIG. 11 is a flowchart illustrating the steps involved in the procedure of localizing individual fiducial markers on the target array (illustrated in this embodiment as LEDs)

The acquired image is compressed in order to more efficiently locate the fiducial markers (in FIG. 9, the fiducial markers are LEDs). The LEDs are then located in the compressed image, and the neighborhood (i.e., general area) of the LED is identified. This neighborhood is scanned in the uncompressed image to identify the exact position of the LEDs. One embodiment of a sequence for locating LEDs is shown in FIG. 11. The foreground and background images are gamma corrected so that the pixel values are proportional to the light intensity of the LED. The gains of the foreground and background are then matched. The background image is then subtracted from the foreground image. A threshold is then applied to the difference image and pixels with intensities above the thresholds are marked as possible candidates for the location of a LED. The LED candidates are traced and analyzed, and candidates that do not meet certain criteria (for example, size, shape, color, intensity, etc.) are discarded. Finally, a list of candidate LED positions is returned to the calling process.

By locating the general position of the LEDs in a compressed image, the speed of the process is greatly increased. Any LEDs in the neighborhood are identified and added to a final list of LED locations. The identification steps are repeated until all four LEDs are located and added to the final list of LED locations. If the final list does not contain exactly four LEDs, the tube measurement process is terminated and an error light displayed. If there are exactly four LEDs in the final list, the tube position is calculated (as shown in FIGS. 9 and 12).

Figure 12:
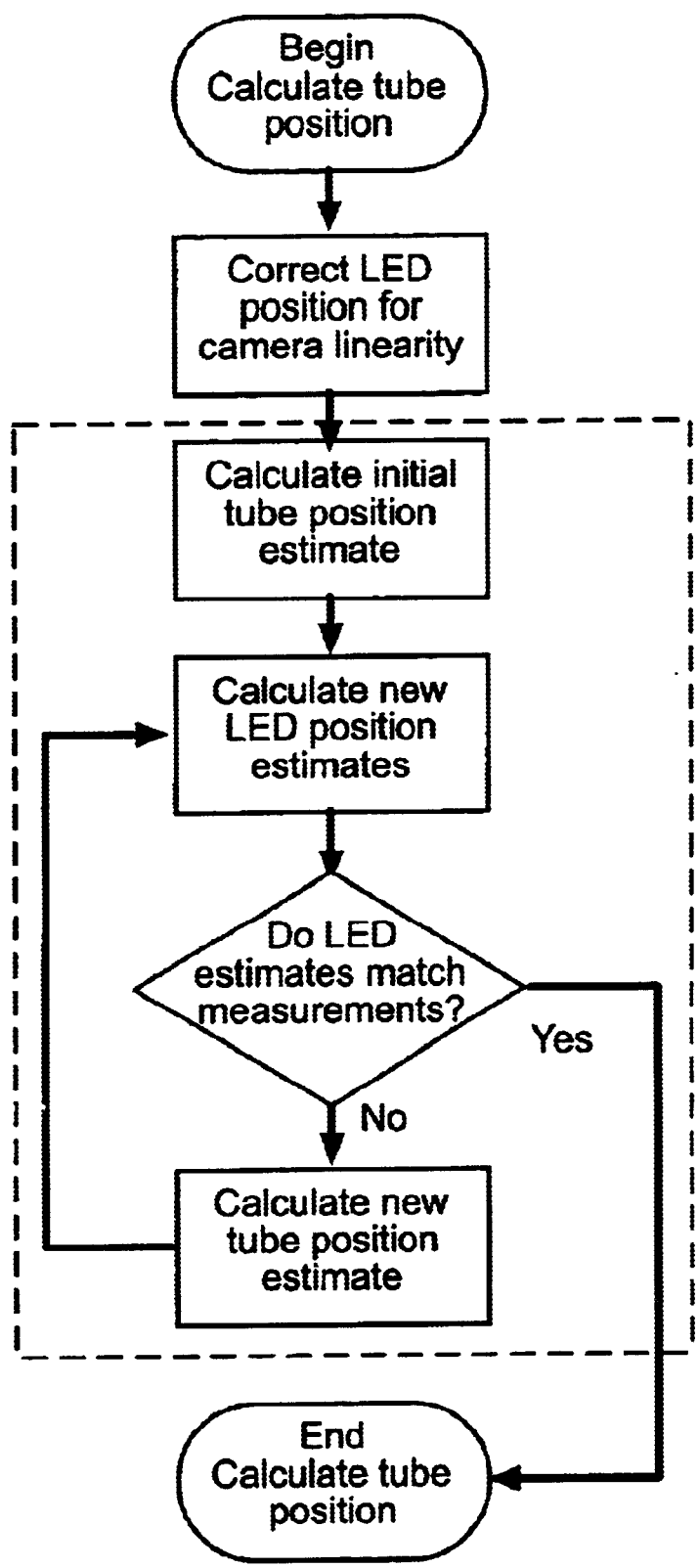
FIG. 12 is a flowchart illustrating the steps involved in calculating the position of the x-ray source assembly.

FIGS. 9 and 12 describe how the LED information is analyzed to determine the position of the camera relative to the LED array (i.e., the fiducial markers 50), and by inference the position and orientation of the tube housing 22 relative to the grid tunnel 30/anti-scatter grid 32. First, the camera linearity calibration is used to convert the centroid of each LED (in pixel units) to a physical position (in cm) projected onto a fiducial image plane. The Marquardt algorithm is used to calculate the position of the LED array relative to the tube housing 22 from these measurements. The Marquardt algorithm is a general iterative algorithm for fitting a non-linear function to a set of data, starting from an initial estimate of the function parameters. The implementation generates the initial estimate by assuming that the distance to the camera is infinite, and that the magnification of the camera image is unknown. The iterations continue until a convergence criterion is reached. The final estimated parameters are considered good if the measured and estimated LED positions match to within some limit (e.g. 0.05 cm). The mathematics involved in the calculation of the algorithm to convert the position measurements of the fiducial markers to a desired position and orientation of the tube housing 22 involve Cartesian coordinate transforms. The details of this field of mathematics are well known to those of ordinary skill in the art.

In response to calculation of the optical position and orientation, the drive means, such as servo motors, located within mobile system 10, position the tube housing 22 to align the x-ray focal spot to an optimal position and orientation for use with the anti-scattering grid 32. In order to be able to exactly match the position and orientation of the anti-scattering grid 32, the x-ray tube housing 22 should have six degrees of freedom, as discussed above. Three degrees of freedom correspond to the three spatial dimensions of the focal spot location, two degrees of freedom correspond to the direction (altitude and azimuth) of the central ray of the X-ray beam, and one degree of freedom corresponds to a rotation of the collimator around the X-ray beam. The MCS should have associated with each degree of freedom of motion of the drive means to drive this motion, and an encoder 29 (either relative or absolute) in communication with the processing means to determine the current position of the components.

Figure 13:
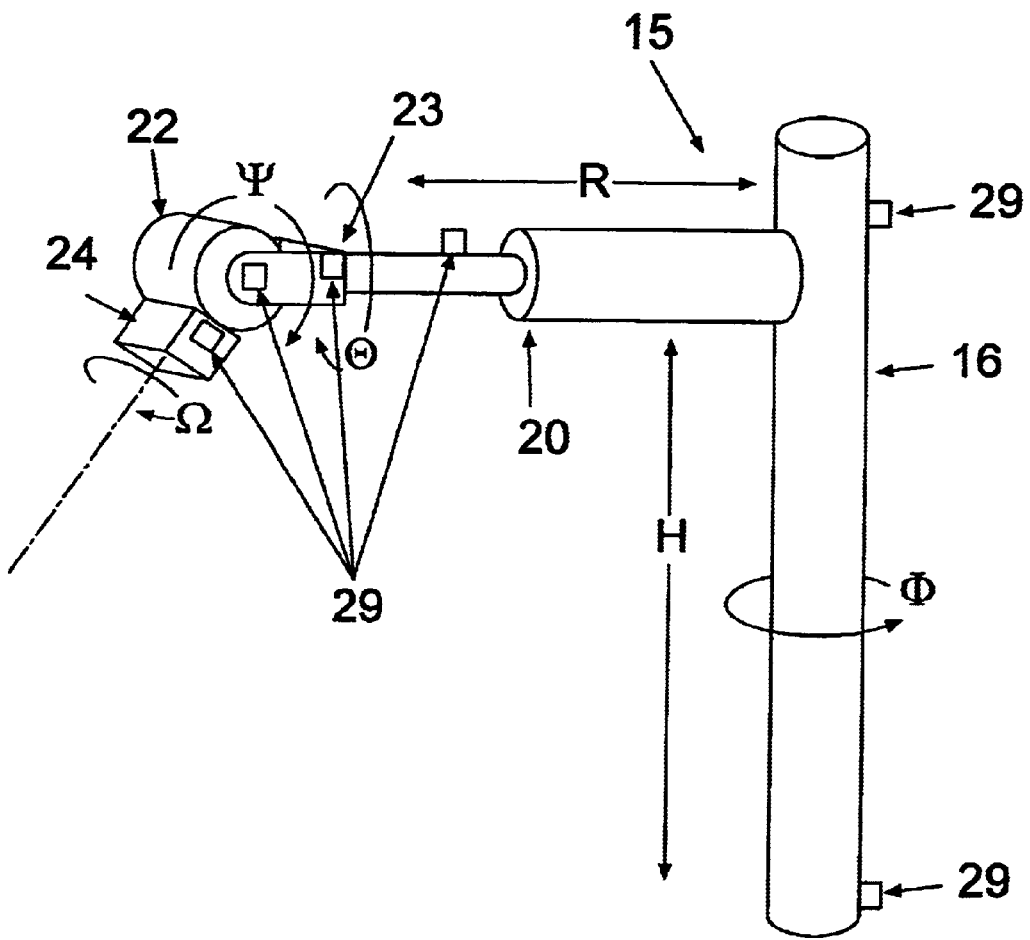
FIG. 13 illustrates one embodiment of the x-ray source assembly showing the different degrees of rotation in each component.

In one embodiment (FIG. 13), the X-ray tube housing 22 is mounted in a gimbal 23. The gimbal 23 is mounted on a horizontal extensible arm 20, which in turn is mounted to a vertical column 16. The X-ray collimator housing 24 is mounted on the x-ray tube housing 22. The arm 20 can be extended or retracted (motion R), moved up and down the column 16 (motion H), and the column can be rotated about a vertical axis (motion $\Phi$). The three motions R, H, and $\Phi$ together provide the three degrees of freedom necessary to locate the center of the gimbal 23 at a given spatial location.

Once the gimbal 23 is located, the two bearings of the gimbal can be rotated (motions $\Theta$ and $\Psi$) defining two additional directional degrees of freedom. If the focal spot is located at the intersection of the axes of motions $\Theta$ and $\Psi$, then its position is determined uniquely by motions H, R, and $\Phi$. Otherwise, the position of the focal spot is determined also by motions $\Theta$ and $\Psi$ as well. The last degree of freedom lies in the rotation $\Omega$ of the collimator housing 24 around the central ray of the X-ray beam.

When the AMS is activated, an image is acquired of the target arm assembly and the desired position and orientation of the X-ray tube assembly is calculated as described above. The AMS then activates the MCS and the drive means direct motions H, $\Phi$, and R to place the gimbal in its desired location. Once the gimbal is in place, the drive means directs the remaining three motions to orient the x-ray beam and collimator properly. These motions could be activated sequentially or in parallel. Sequential activation would have the advantage of reduced alignment time, but the disadvantage of increased cost and possible distraction of the technologist by a relatively complex motion.

Optionally, the operating console 14 is equipped with an inner lock disabling the x-ray exposure until the x-ray focal spot and grid have been aligned according to the present invention. Further, it is appreciated that an increase in tube voltage is expected to provide improved images as compared to imaging done absent an anti-scattering grid. The increase in tube voltage is intended to increase x-ray transmission through the patient 1 and thereby allow a shorter exposure time. Optionally, a mobile x-ray system according to the present disclosure is provided with an alarm system which is activated upon movement of the system 10 absent grid tunnel 30 to prevent accidental loss of the grid tunnel 30 and the target arm 28.

It is appreciated that localization techniques can be performed not only by the optical methods detailed herein, but also through the use of magnetic dipole technology, ultrasound technology, direct mechanical sensing, and internal navigation technology. Magnetic dipole arrays and sensors operating with the benefit of current loops or electromagnets are detailed in U.S. Pat. No. 4,054,881.

Inertial navigation technology would differ from other technologies described in that it would independently measure motion of the grid tunnel and either the console or tube housing, producing measurements of the absolute positions of these devices rather than the position of one relative to another. As the process of determining a relative position from two absolute positions is well established, the use of this technology would be essentially the same as for the others. It is possible to manufacture inertial navigation units (INU) 31 (FIG. 13) small enough for this application using MEMS (Micro-electromechanical system) technology. Such units can incorporate acceleration sensors, rotation sensors, or both.

The motion of the grid tunnel could be tracked by a single attached INU with 3 acceleration sensors and 3 rotation sensors, or by 3 INUs with two acceleration sensors per INU attached to 3 corners of the grid tunnel, or by other similar combinations. The position of the grid tunnel would then be calculated by tracking its motion from the moment it leaves a mount fixed to the side of the mobile radiographic system console. To track the position of the source assembly one could mount INUs on it. Alternately, one could track the position of the console by mounting INUs in it and then calculate the position of the source assembly using the readings from the MCS. Finally, one could lock the wheels of the console after the grid tunnel is removed from its mount, and assume that the console remains stationary.

It is also appreciated that while the invention as described here provides closed loop control of the x-ray source assembly position and orientation, it is also possible to use open loop control. In this approach, the measurement means is equipped with a display that provides the user with information that directly or indirectly describes the position and orientation of the grid tunnel relative to the x-ray source assembly. The measurement means could be digital, such as the camera/target array system described here, or analog, such as the system described by Niklason ([2]Niklason et al., *Med. Phys.* 8:677–681, 1981). Such analog techniques are known in the prior art, and are described in the references. The user then uses this information to control an automatic motion control system to move the x-ray source assembly to an aligned position. For example, the unit could be equipped with a control module, a mechanical linkage between the source assembly and the grid tunnel, and a series of dials mechanically attached to the linkage which indicates the degree of misalignment. The user controls the MCS through the control module, moving the x-ray focal spot until all the dials indicate a value of zero, which indicates alignment. Alternately, the unit could be equipped with an automatic measurement system, a digital display that indicates the degree of misalignment, and a keypad connected to a computer that controls the MCS. The user would enter the displayed numbers on the keypad, and the computer would then calculate the position required to achieve alignment and direct the MCS to move the x-ray focal spot to this position. These examples are mean to illustrative, and are not an exhaustive catalog of open-loop control approaches to achieving alignment. Such approaches are inferior to the closed-loop control approach and require more effort on the part of the user to align the source assembly and grid.

Patents and publications mentioned in this specification are indicative of the levels of those skilled in the art to which the disclosure pertains. These patents and publications are incorporated herein by reference to the same extent as if each individual patent or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

REFERENCES

1. Barnes G T: Contrast and Scatter in X-Ray Imaging. *RadioGraphics* 11:307–323, 1991.
2. Niklason L T, Sorenson J A, Nelson J A: Scattered Radiation in Chest Radiography. *Med. Phys.* 8:677–681, 1981.
3. Tucker D M, Souto M, Barnes G T: Scatter in Computed Radiology. *Radiology* 188:271–274, 1993.
4. Niklason L T, Barnes G T, Carson P: Accurate Alignment Device for Portable Radiography. *Radiology* 173 (P):452, 1989.
5. O'Donovan P B, Skipper G J, Litchney J C, Salupo A J, Bortnick J R: Device for Facilitating Precise Alignment in Bedside Radiography. *Radiology* 184:284–285, 1992.
6. Press W H, Flannery B P, Teukolsky S A, Vetterling W T, Numerical Recipes in C: The Art of Scientific Computing, Cambridge University Press, Cambridge UK, 1988.

What is claimed is:

1. A mobile radiographic system, the system comprising:
   a. an x-ray source assembly comprising an x-ray tube housing having an x-ray source with a focal spot, and an x-ray collimator coupled to the tube housing;
   b. a tube housing mounting that supports the x-ray source assembly and has a plurality of degrees of freedom to allow the x-ray tube housing to be moved to a desired position and desired orientation;
   c. an anti-scatter grid, said anti-scatter grid and image receptor not being in a fixed orientation relative to the x-ray source;
   d. a measuring means to determine the position of the anti-scatter grid and image receptor relative to a fixed point on the mobile radiographic system;
   e. a motion control system to control the position and orientation of the x-ray source assembly relative to the anti-scatter grid and an image receptor, the motion control system comprising a drive means for at least one degree of freedom of motion in the tube housing mounting and x-ray source assembly and a means for determining the position of the x-ray source assembly relative to a console of the mobile radiographic system; and
   f. a processing means in communication with the measuring means and the motion control system.

2. The system of claim 1 where the means for determining is in communication with the processing means and is selected from the group consisting of at least one encoder for each degree of freedom of motion in the tube housing mounting and x-ray source assembly and at least one inertial navigation unit on the x-ray source assembly.

3. The system of claim 1 where the measuring means is an automatic measuring system, the automatic measuring system comprising a grid tunnel and a detecting means mounted to the mobile radiographic system, the grid tunnel comprising the anti-scattering grid, the image receptor and an external object.

4. The system of claim 3 where the external object comprises a target array, the target array being removably coupled to the grid tunnel by a rigid arm and the target array comprising a plurality of fiducial markers, and where the detecting means is capable of generating an image of the fiducial markers on the target array.

5. A The system of claim 1 where the measuring means is an automatic measuring system, the automatic measuring system comprising a grid tunnel and one or more inertial navigation units attached to the grid tunnel, and optionally one or more inertial navigation units attached to the mobile radiographic system, the inertial navigation units on the grid tunnel and the inertial navigation units on the mobile radiographic system being in communication with the processing means, the inertial navigation units being selected from the group consisting of inertial navigation units having an acceleration sensor and a rotation sensor and inertial navigation units having an acceleration sensor.

6. The system of claim 1 where the measuring means is an automatic measuring system, the automatic measuring system comprising a direct mechanical linkage between the grid tunnel and the mobile radiographic system, the mechanical linkage being in communication with the processing means.

7. The system of claim 3 where the anti-scattering grid is incorporated into the grid tunnel and the grid tunnel has an internal cavity for receiving the image receptor.

8. The system of claim 3 where the detecting means is selected from the group consisting of an optical detector and an ultrasound detector.

9. The system of claim 3 where the detecting means is selected from the group consisting of a magnetic detector.

10. The system of claim 8 where the optical detector is selected from the group consisting of: a still frame digital camera, a digital video camera, and an analog video camera.

11. The system of claim 4 where the processing means receives the image of the fiducial markers on the target array from the detecting means, determines the position and orientation of the fiducial markers from the image, and calculates the position and orientation of the target array relative to the position and orientation of the detecting means from the position and orientation of the fiducial markers.

12. The system of claim 11 where the processing means uses the position and orientation of the target array relative to the position and orientation of the detecting means to direct the drive means to position the x-ray source assembly so that the focal spot is in the state of alignment with respect to the focal line of the anti-scattering grid.

13. The system of claim 12 where the state of alignment is selected from the group consisting of an optimal state of alignment, and an acceptable state of alignment.

14. The system of claim 13 where the grid tunnel further comprises a sensing means to determine the orientation of the long axis of the grid tunnel relative to the target arm and to communicate the orientation of the long axis of the grid tunnel to the processing means.

15. The system of claim 14 where the processing means directs a drive means in communication with the collimator to automatically orientate the collimator along the long axis of the grid tunnel and automatically directs a drive means in communication with the collimator blades to adjust the width and length of the x-ray beam to substantially match the orientation of the image receptor.

16. The system of claim 15 where 2 degrees of freedom of the motion control system position the focal spot substantially on the focal line of the anti-scattering grid.

17. The system of claim 16 where 1 additional degree of freedom of the motion control system positions the focal spot substantially at the center of the focal line of the anti-scattering grid.

18. The system of claim 17 where 2 additional degrees of freedom of the motion control system align the central ray substantially on the center of the anti-scattering grid.

19. The system of claim 18 where 1 additional degree of freedom of the motion control system aligns the collimator with the long axis of the grid tunnel.

20. The system claim 19 where the x-ray source assembly further comprises an adjustable vertical column and an adjustable horizontal arm attached to the vertical column, the x-ray tube housing being mounted to the horizontal aim by an adjustable gimbal.

21. The system of claim 19 where the motion control system positions the x-ray source assembly to a state of alignment in a sequential manner.

22. The system of claim 19 where the motion control system positions the x-ray source assembly to a state of alignment in a parallel manner.

23. The system of claim 10 where the fiducial markers are selected from the group consisting of colored LEDs and monochrome LEDS.

24. The system of claim 23 where there are at least four fiducial markers on the target array, the fiducial markers separated from one another by a known distance.

25. The system of claim 24 where the fiducial markers are not located in any single plane.

26. The system of claim 3 where the anti-scattering grid is a high ratio anti-scattering grid.

27. The system of claim 12 further comprising a display means to inform the operator, directly or indirectly, of the condition of the system.

28. The system of claim 27 where the display means is selected from the group consisting of a plurality of indicator lights and a display panel, and the condition of the system represents the state of alignment of the system.

29. The system of claim 27 further comprising a control means on the x-ray source assembly by which the user can activate the motion control system to direct the x-ray source assembly to a state of alignment.

30. The system of claim 29 where the control means selected from the group consisting of a button and a toggle switch and where the operator is required to continually depress the control means for the motion control system to remain active.

31. The system of claim 1 where the measuring means is an analogue measuring system, and the analogue measuring system further comprises an alignment means and a grid tunnel, the grid tunnel comprising the anti-scattering grid, the image receptor and an external object.

32. The system of claim 31 where the alignment means indicates when the x-ray source assembly is in a state of alignment with reference to the anti-scattering grid.

33. The system of claim 32 where the state of alignment is selected from the group consisting of an optimal state of alignment and an acceptable state of alignment.

34. The system of claim 33 where the operator activates the motion control system to direct the x-ray source assembly to a state of alignment.

35. The system of claim 34 where the operator manually orientates the collimator so the collimator is orientated along the long axis of the grid tunnel and the collimator blades adjust the width and length of the x-ray beam to substantially match the orientation of the long axis of the grid tunnel and the associated image receptor.

36. The system of claim 34 where the operator activates the motion control system to orientate the collimator so the collimator is orientated along the long axis of the grid tunnel and the collimator blades are adjust the width and length of the x-ray beam to substantially match the orientation of the long axis of the grid tunnel and the associated image receptor.

37. The system of claim 35 where the system is an open loop system.

38. The system of claim 36 where the system is an open loop system.

39. The system of claim 35 where 2 degrees of freedom of the motion control system position the focal spot substantially on the focal line of the anti-scattering grid.

40. The system of claim 39 where 1 degrees of freedom of the motion control system positions the focal spot substantially at the center of the focal line of the anti-scattering grid.

41. The system of claim 40 where 2 additional degrees of freedom of the motion control system align the central ray substantially on the center of the anti-scattering grid.

42. The system of claim 41 where 1 additional degree of freedom of the motion control system aligns the collimator substantially with the long axis of the grid tunnel.

43. The system of claim 42 where the x-ray source assembly further comprises an adjustable vertical column and an adjustable horizontal arm attached to the vertical column, the x-ray tube housing being mounted to the horizontal arm by an adjustable gimbal.

44. The system of claim 42 where the motion control system positions the x-ray source assembly to a state of alignment in a sequential manner.

45. The system of claim 42 where the motion control system positions the x-ray source assembly to a state of alignment in a parallel manner.

46. The system of claim 34 further comprising a display means to inform the operator, directly or indirectly, of the condition of the system.

47. The system of claim 46 where the display means is selected from the group consisting of a plurality of indicator lights and a display panel, and the condition of the system represents the state of alignment of the system.

48. The system of claim 46 further comprising a control means on the x-ray source assembly by which the user can activate the motion control system to direct X-ray source assembly to a state of alignment.

49. The system of claim 48 where the control means selected from the group consisting of a button and a toggle switch and where the operator is required continually depress the control means for the motion control system to remain active.

50. The system of claim 31 where the external object is a target array removably coupled to the grid tunnel and the target array comprises a plurality of fiducial markers.

51. The system of claim 50 where the fiducial markers are selected from the group consisting of LEDs.

52. The system of claim 50 where there are at least 4 fiducial markers on the target array separated from one another by a known distance and the fiducial markers are not located in any single plane.

53. The system of claim 31 where the anti-scattering grid is a high ratio anti-scattering grid.

* * * * *